United States Patent [19]
Pye

[11] Patent Number: 5,592,296
[45] Date of Patent: Jan. 7, 1997

[54] EXHAUST GAS PARTICLE SENSOR

[75] Inventor: John A. Pye, Essex, United Kingdom

[73] Assignee: GEC-Marconi Limited, Middlesex, United Kingdom

[21] Appl. No.: 574,558

[22] Filed: Dec. 14, 1995

Related U.S. Application Data

[63] Continuation of Ser. No. 963,488, Oct. 20, 1992, abandoned.

[30] Foreign Application Priority Data

Oct. 22, 1991 [GB] United Kingdom ............... 9122361

[51] Int. Cl.$^6$ ........................ G01N 21/15; G01N 21/59
[52] U.S. Cl. ........................ 356/435; 356/437; 356/438
[58] Field of Search ....................... 356/38, 436, 437, 356/438, 432, 439, 440, 441, 435

[56] References Cited

U.S. PATENT DOCUMENTS

| | | | |
|---|---|---|---|
| 3,711,210 | 1/1973 | Krukowski | 356/438 |
| 3,743,430 | 7/1973 | Riggs | 356/207 |
| 3,833,305 | 9/1974 | Porter et al. | 356/438 |
| 3,850,529 | 11/1974 | Brugger . | |
| 3,895,233 | 7/1975 | Boll et al. | 356/435 X |
| 3,958,122 | 5/1976 | Jowett et al. | 250/346 |
| 3,967,904 | 7/1976 | Cade . | |
| 3,973,852 | 8/1976 | Moore et al. | 356/438 |
| 3,997,271 | 12/1976 | Brugger et al. . | |
| 4,087,690 | 5/1978 | Prober | 250/343 |
| 4,544,273 | 10/1985 | Berndt | 356/434 |
| 4,583,859 | 4/1986 | Hall, II | 356/438 |
| 4,713,964 | 12/1987 | Ioannides | 73/116 |
| 4,785,170 | 11/1988 | Witt . | |
| 4,937,461 | 6/1990 | Traina | 250/575 |

FOREIGN PATENT DOCUMENTS

| | | |
|---|---|---|
| 0076338 | 5/1981 | European Pat. Off. . |
| 2498024 | 1/1981 | France . |
| 2544592 | 7/1976 | Germany . |
| 56-132035 | 10/1981 | Japan . |
| 2165694 | 4/1986 | United Kingdom . |
| 2186112 | 8/1987 | United Kingdom . |
| 2252621 | 8/1992 | United Kingdom . |

*Primary Examiner*—Vincent P. McGraw
*Attorney, Agent, or Firm*—Donald C. Casey

[57] ABSTRACT

In a exhaust smoke sensor a light emitter generates a light beam which passes through a region containing the exhaust gas to a first light sensor. To reduce interference the light emitter is driven by a near square wave signal produced by passing a square wave through a low pass filter.

9 Claims, 4 Drawing Sheets

EXHAUST GAS PARTICLE SENSOR

This application is a continuation of application Ser. No. 07/963,488 filed Oct. 20, 1992, now abandoned.

BACKGROUND OF THE INVENTION

This invention relates to an exhaust gas particle sensor and in particular to a vehicle exhaust smoke sensor.

Increasingly legislation is being enacted to set limits on vehicle exhaust smoke, particularly from diesel engined vehicles.

It has been proposed in our co-pending patent application Ser. No. 9105731 that levels of smoke or other particles in vehicle exhausts could be sensed by measuring the opacity of the exhaust gases.

The opacity is measured by passing a light beam across a chamber through which the exhaust gases are flowing and measuring the reduction in the intensity of the light beam after its passage through the chamber.

For compression ignition engines, also known as diesel engines, the current UK exhaust smoke limit is defined as an absorption coefficient of $3.2 \ m^{-1}$.

A common type of opacity measurement system is where a light source and a main light sensor are placed on opposite sides of a sensing chamber. The intensity of a light beam from the light source incident on the light sensor is measured with only clean air in the sensing chamber, and then measured again with the exhaust gases in the sensing chamber. By comparing the two intensities the opacity of the exhaust gases can be calculated.

In such opacity measuring systems it is known to provide a monitoring light sensor which measures the intensity of the light beam generated by the light emitter before the light beam enters the sensing chamber. By comparing this measurement of intensity when air only is in the sensing chamber with a measurement of intensity of the light beam before the light beam enters the sensing chamber with exhaust gases in the sensing chamber, any changes in the intensity of the light beam generated by the light emitter can be compensated for. Generally where the light emitter is a light emitting diode and the sensors are photodiodes the monitoring light sensor is mounted adjacent the light emitter on a common header.

In theory such an arrangement should allow the opacity to be measured with great accuracy because any difference in the intensity of the light beam produced by the light emitter can be compensated for, leaving only the intensity differences produced by the opacity of the exhaust gases within the chamber. Furthermore, if the monitoring light sensor and the main light sensor are of the same type and processed by identical processing electronics it is possible to use the signals generated by the monitoring light sensor to compensate for changes in sensor efficiency or in the gain and efficiency of the processing circuits due to external parameters such as temperature. In practice however it has been found that where the light emitter and monitoring light sensor are placed on a common header and enclosed by a common enclosure light from the light emitting diode only reaches the photodiode after reflection from the enclosure and other parts of the optical system. As a result, otherwise trivially small relative movements of the parts of the optical system reflecting this light can cause sudden changes in the light intensity received by the photodiode. This is interpreted as a change in the light intensity produced by the light emitter and in attempting to compensate for this a change in opacity may be registered without any change in opacity having occurred.

This is a problem because it prevents an accurate measurement of opacity being produced.

Another problem encountered in optical opacity measurement systems is that external light sources impinging on the detectors can produce erroneous measurements of opacity because they interfere with measurement of light intensity. It is has been proposed to overcome this problem by employing a modulated light source and filtering the signals produced by the photodetectors to eliminate signals due to ambient light.

The problem with conventional filters is that their characteristics, including gain, are affected by the temperature coefficient of their components. Normal practice would be for the AC signal generated by the photodetector to be converted to DC and then sampled by an analogue to digital converter. This has the disadvantage that any residual noise in the signal will be added to the DC signal, thus producing an error.

This invention was made in an attempt to produce an exhaust gas particle sensor at least partially overcoming these problems.

BRIEF SUMMARY OF THE INVENTION

In a first embodiment this invention provides an exhaust gas particle sensor comprising a light source and a light sensor in which the opacity of gas is measured by passing a light beam emitted by the light source through the gas and the intensity of the light beam emitted by the light source is varied in a near square wave waveform.

A near square wave is a waveform approximating to a square wave but having a short but finite time taken to go from its low state to its high state and vice-versa rather than moving from one state to another instantaneously.

The modulated light beam allows the effects of ambient unmodulated light to be eliminated using well known signal processing techniques.

If a sine wave modulation was used any error in time synchronisation of sampling the intensity levels of the light beam before and after it passes through the gas would result in an erroneous opacity measurement. This is avoided by using a square wave type modulation having a constant upper and lower value for a significant fraction of each cycle.

A pure square wave would have the disadvantages that it would have a DC component and that the very fast edge required by the change of state between peak and trough would require circuitry with a very high frequency response and could be radiated and picked up by different parts of the circuit, generating interference.

All of these possible disadvantages can be avoided by using a near square wave waveform to modulate the light beam. The preferred waveform is a square wave that has been passed through a low pass filter.

In a second embodiment this invention provides an exhaust gas particle sensor which measures the opacity of a gas by passing a light beam through the gas in which the light beam is generated by a light emitting diode, the intensity of the light beam is sensed by a first photodiode after it has passed through the gas and including a second photodiode arranged to sense the intensity of the light beam before it passes through the gas, the light emitting diode being mounted on a header and the second photodiode being mounted on a rigid extension of the same header such that a part of the light emitted by the light emitting diode is directly incident on the second photodiode.

This allows the second, or monitoring, photodiode to be held rigidly in a fixed position relative to the light emitting diode without being dependent on reflected light.

BRIEF DESCRIPTION OF THE DRAWINGS

A sensor embodying the invention will now be described by way of example only with reference to the accompanying diagramatic Figures in which.

DETAILED DESCRIPTION

Figure 1:
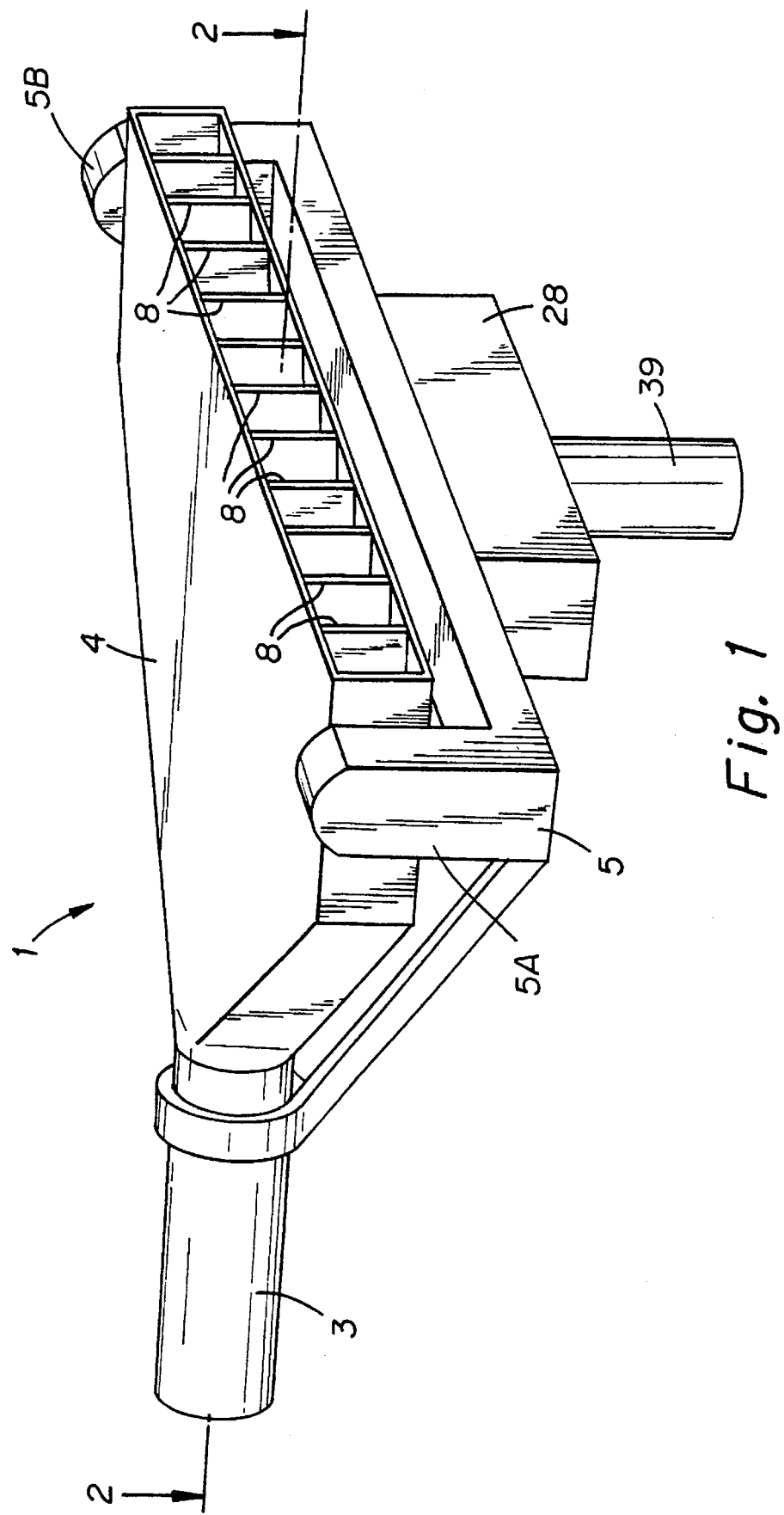
FIG. 1 shows a perspective view of a vehicle exhaust particle sensor according to the invention.
Figure 2:
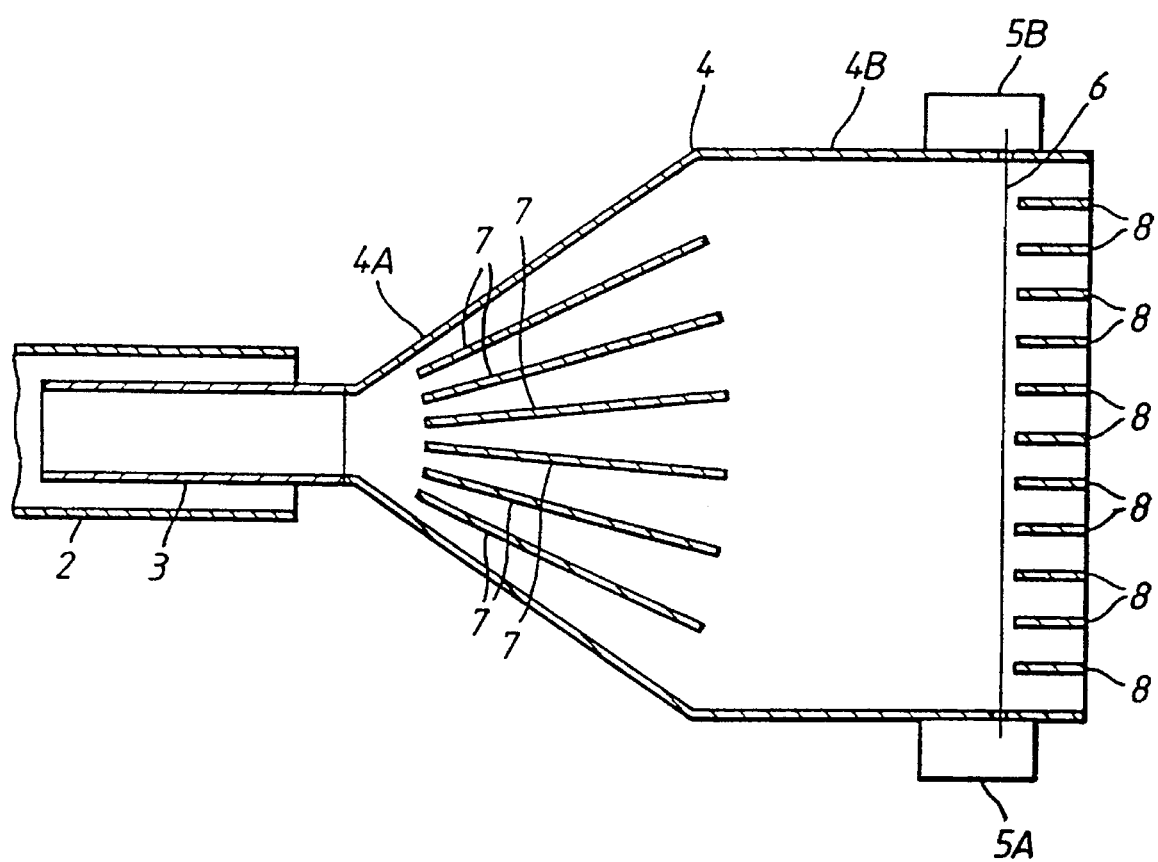
FIG. 2 shows a cross sectional view through the sensor of FIG. 1 along the line 2—2 in FIG. 1.
Figure 3:
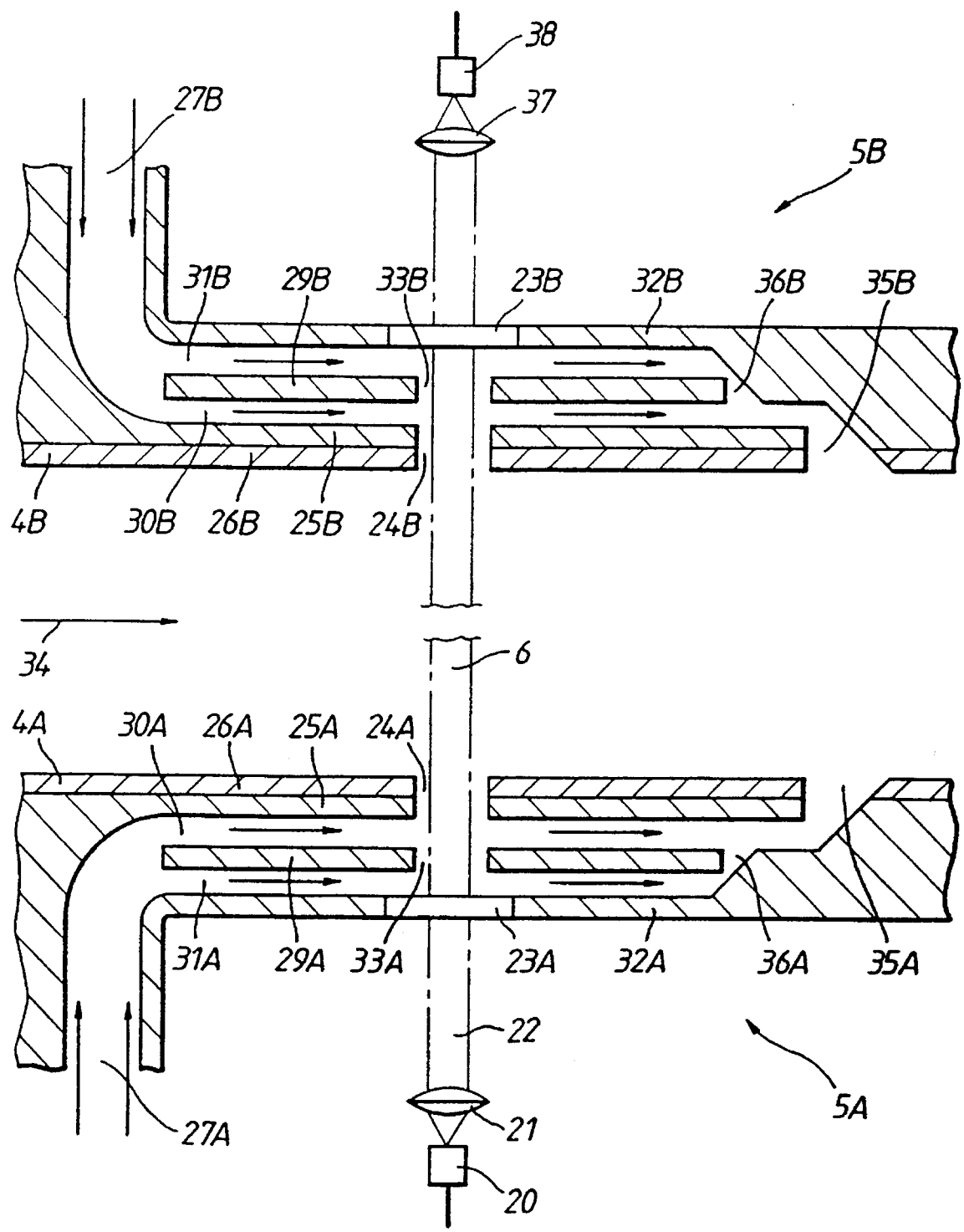
FIG. 3 shows a more detailed view of a part of the cross section of FIG. 2.

Referring to FIGS. 1 to 3 an exhaust gas particle sensor 1 is shown, this is intended to measure particle levels in exhaust gases from an exhaust pipe 2 by measuring the opacity of the exhaust gases. The particle sensor 1 has three main parts, an input tube 3, a sensing portion 4 and a substantially 'U' shaped main body 5. The main body 5 is rigidly attached to the input tube 3, while the sensing portion 4 is releasably attached to the main body 5 and input tube 3.

The input tube 3 is circular and has a diameter of 25 mm so that, in use, it can be inserted into the end of a vehicle exhaust pipe 2. The narrowness of the input tube allows it to fit into a very wide range of sizes of exhaust pipe. Since the input tube 3 is placed inside the vehicle exhaust pipe 2 only undiluted exhaust gases are taken into the sensor 1.

The input tube 3 is rigid and short, the input tube 3 is short to reduce the tendency of particles in the exhaust gases to stick to the sides of the input tube 3 or agglomerate, both of which would tend to reduce the measured opacity of the exhaust gases.

The sensing portion 4 comprises a transition section 4A immediately downstream of the input tube 3 and a constant area portion 4B of rectangular cross section downstream of the transition section 4A. The constant area portion 4B forms a gas duct 100 mm wide and 10 mm high, that is a two fold increase in cross-sectional area over the input tube 3, and the transition section 4A forms a smooth transition between the input tube 3 and the constant area portion 4B. The opacity of the exhaust gases is measured as it passes through the constant area portion 4B. This arrangement is used because if the sensor had the same cross section throughout the small diameter of the input tube 3 would only give a very short optical path length for opacity measurement, by measuring opacity across the constant area portion 4B a quadrupled optical path length is provided.

The U shaped body 5 has two uprights 5A and 5B. Opacity measurement is carried out using a light beam produced within the upright 5A, passing through the constant area portion 4B and being received in the upright 5B along an optical path 6.

In the transition portion 4A a first plurality of baffles 7 are provided. The baffles 7 extend right across the transition portion 4A and modify the exhaust gas flow through the transition portion 4A so that the time taken for a wavefront in the exhaust gas to travel from the upstream end of the transition portion 4A to the optical path 6 is substantially a constant across the whole width of the exhaust gas flow. The time taken will of course vary depending on the pressure and flow rate of the exhaust gases, but the important thing is that at any given exhaust gas pressure and flow rate the time taken is independent of position across the gas flow.

If the first baffles 7 were not provided, the velocity of gas in the central region of the transition portion 4A would be greater than at the edges so that if a pulse of smoke was present in the exhaust gases entering the transition portion 4A it would be spread out along the flow of exhaust gases resulting in a reduced opacity value as the smoke crosses the optical path 6.

The time taken is referred to as substantially constant since there will still be boundary layer effects at the edges of the transition portion 4A and the constant volume portion 4B, but the effect of these is insignificant compared to the effects that would be produced by the transition if the baffles 7 were not present.

A second set of 11 baffles 8 are provided downstream of the optical path 6 at the downstream end of the constant area portion 4B. These baffles extend across the constant area portion 4B and divide it into 12 parallel sided gas flow channels of equal size.

The baffles 8 prevent any wind past the sensor 1 blowing clean air into the constant volume portion 4B and into the optical path 6. If this occurred it would of course make the opacity measurement unreliable.

The baffles 8 prevent such clean air entering the optical path 6 because they reduce the lateral dimension of any swirl generated by wind and so reduce the distance which any wind generated swirl will penetrate into the constant area portion 4B.

Referring to FIG. 3 the uprights 5A and 5B of the main body 5 are shown in more detail. Inside the upright 5A is a light emitter 20 and a lens 21 arranged to produce a light beam 22 which follows the light path 6. The light beam 22 passes through a protective window 23A in a wall 32A within the upright 5A and an aperture 24A in a wall 25A of the upright 5A and a wall 26A of the constant area portion 4B into the exhaust gases within the portion 4B.

In order to prevent particles from the exhaust gases being deposited on the window 23A a dual air curtain is provided. Clean air under pressure is provided along a clean air duct 27A. This air comes from a compressor 28 which includes an electrostatic precipitator (not shown) which filters the air to remove any smoke and other particles in the ambient air before it is passed along the clean air duct 27A.

A wall 29A divides the clean air duct 27A into a first clean air passage 30A and a second clean air passage 31A, the first clean air passage 30A is defined between the wall 29A and the wall 25A while the second clean air passage 31A is defined between the wall 29A and the wall 32A. The wall 29A has an aperture 33A to allow the light beam 22 to pass through it.

The airflow along the two clean air passages 30A and 31A is parallel to the direction of flow of exhaust gases through the constant area portion 4B, denoted by the arrow 34. This parallel flow helps to reduce the tendency for clean air plumes to be injected into the constant area portion 4B. The two clean air passages 30A and 31A recombine downstream of the optical path 6 and the clean air flow is dumped into the exhaust gas flow through an opening 35A. Before the two clean air passages 30A and 31A recombine there is a constriction 36A in the second clean air passage 31A, so that the air pressure within the second clean air passage 31A is always greater than the air pressure within the second clean air passage 30A. As a result there is a pressure differential across the aperture 33A generating a flow of clean air from the second clean air passage 31A into the first clean air passage 30A. When there is a leakage of exhaust gases from the constant area portion 4B into the first clean air passage 30A the exhaust gases are prevented from reaching the window 23A by the higher pressure in the second clean air passage 31A and the exhaust gases are carried away down the first clean air passage 30A.

When the "free-acceleration" test is used the clean air pressure in the first clean air passage 30A need not be as high as in prior art single air curtain systems because some leakage of exhaust gases into the first clean air passage 30A can be tolerated when the engine is running at full speed and the exhaust gases are at a high pressure without any contamination of the window 23A. As a result when the engine is running at a lower speed or idling and the exhaust gas pressure is reduced it is less likely that clean air will escape into the constant volume portion 4B and produce a clean air plume along the optical path 6.

A similar air curtain system, denoted by the letter B in FIG. 3, is used in the second upright 5B to prevent particle deposition on a window 23B. Behind the window 23B is a lens 37 arranged to focus the light beam 22 onto a photosensor 38.

By comparing the intensity of the light beam 22 incident on the photodetector 38 when exhaust gases are present in the chamber 10 with the intensity of the light beam 22 incident on the photodetector 38 when only clean air is present in the chamber 10 the opacity of the gases along the optical path 6 within the constant area portion 4B can be calculated, as is known from patent application Ser. No. 9105731.

A handle 39 is secured to the main body 5 to allow the sensor 1 to be held in position with the input tube 3 inside a vehicle exhaust pipe 2. Power for the compressor 25, light emitter 20, photodetector 38 and associated electronics is provided by batteries attached to the main body 5. This allows the sensor 1 to be readily portable for spot-checks of vehicles, but if it is to be used in one place only a lead to plug into mains power or a seperate power pack could be used.

The sensing portion 4 of the particle sensor is located against the input tube 3 by a push fit seal formed by a resilient gasket, and is releasably attached to the main body 5 by two catches (not shown), one on each of the uprights 5A and 5B. This allows the sensing portion to be removed and replaced as needed in the event of damage or to allow cleaning out of soot deposited from the exhaust gases.

To allow calibration of the sensor 1 the sensing portion 4 can be removed and an optical filter having a known opacity can be placed in the light path 6.

It would also be possible to use a number of different sensing portions for different engines is this desirable if, for example, the differences in exhaust gas pressures would otherwise be too great for the sensor to cope with.

Since all of the optical components are housed in the main body 5 the removal and replacement of the sensing portion 4 for whatever reason will not necessitate the realignment or adjustment of any of the optical components.

Figure 4:
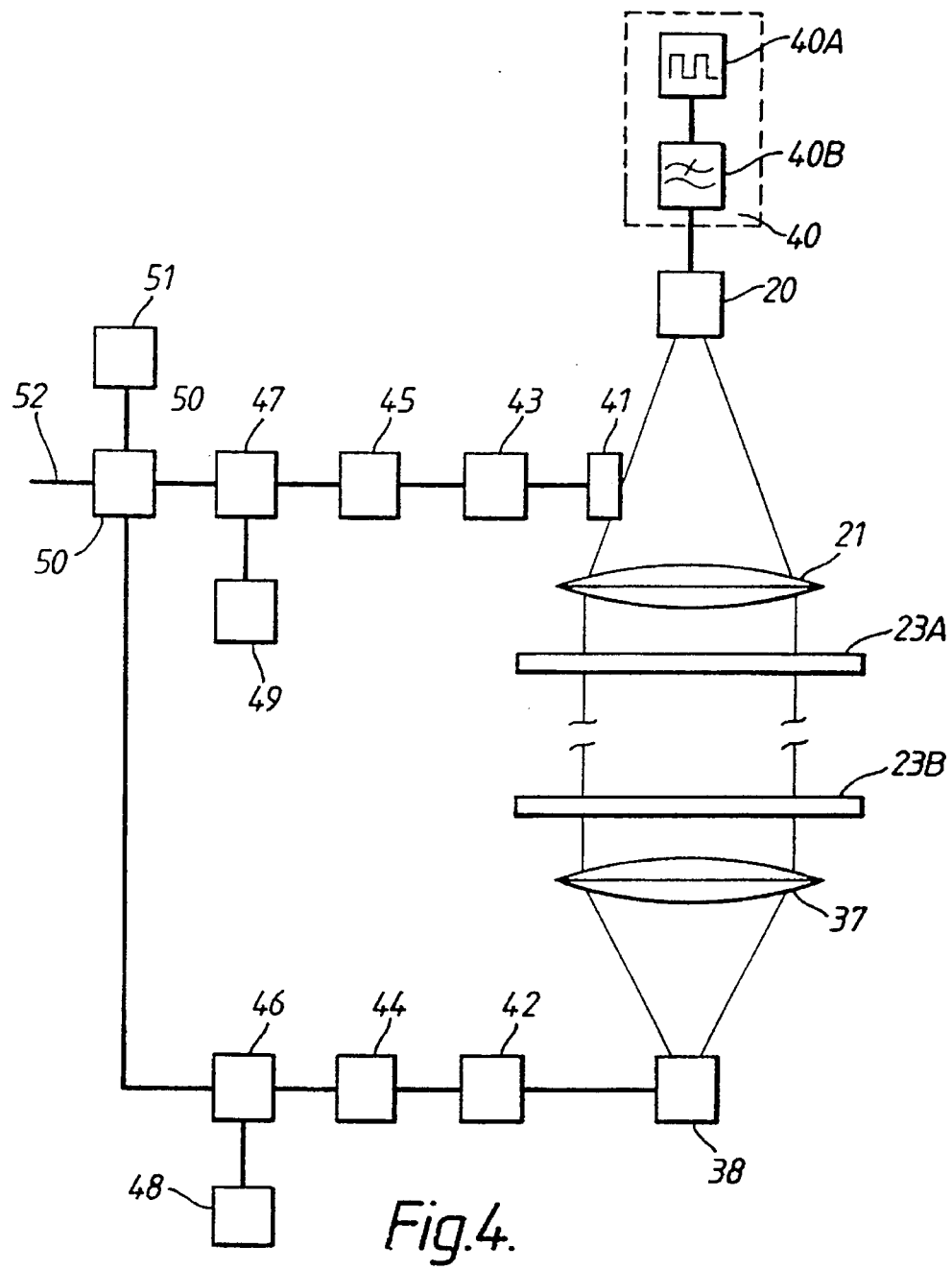
FIG. 4 shows a diagram of the optical opacity measurement system used in the sensor of FIG. 1 and its associated electronics.

Referring to FIG. 4 the arrangement of the light emitter 20 and photodetector 38 and their associated driving and analysis electronics are shown in more detail. The light emitter 20 is a light emitting diode and is driven by a near square wave waveform generator 40. The light generated by the light emitting diode 20 is formed into a beam by a lens 21 and then passes through window 23A into the sensing portion 4. A monitoring photodiode 41 is mounted so that a portion of the light produced by the light emitting diode 20 falls upon it.

Figure 5:
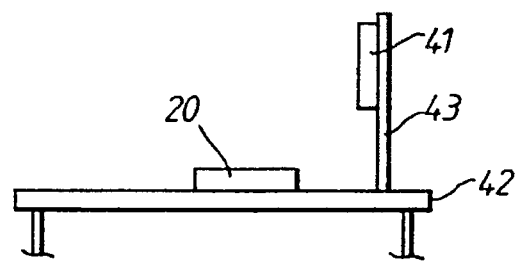
FIG. 5 shows the mounting method of a light emitter and photodetector used in the opacity measurement system of FIG. 4, identical parts having the same reference numerals throughout.

The arrangement of the photodiode 41 is shown in more detail in FIG. 5. The light emitting diode 20 is mounted on a semiconductor header 42 and the photodiode 41 is mounted on a rigid extension 43 orthogonal to the header 42 such that the light emitted by the light emitting diode 20 impinges directly on the photodiode 41.

After passing through the sensing chamber 4 the light beam passes through the window 23B and is focused onto a photodiode 38 by a lens 37.

The signals produced by the two photodiodes 38 and 41 are amplified by two amplifiers 42 and 43 respectively and are then digitised by two analogue to digital converters 44 and 45 respectively, which sample the peaks and troughs of the signals and supply these samples to processors 46 and 47 respectively. The processors 46 and 47 store the samples in associated memories 48 and 49 respectively and average the peak values over four near square wave cycles and averages the trough values of the four cycles to produce an average peak value and an average trough value. As a result of this digitisation and averaging process any noise errors will tend to average out to zero, so this averaging filters noise out of the signal.

These averaged peak and trough values are then subtracted from one another in the processors 46 and 47 to obtain averaged amplitude values.

The averaging process operates as a running average whereby each set of values is averaged with the three preceding values. This averaging does not reduce the accuracy of the opacity measurement provided that the frequency of the near square wave waveform and the sampling is sufficiently high.

Because the light emitting diode 20 is driven with a near square wave waveform small errors in the sampling time will not affect the measured level of light intensity, whereas if a conventional sine wave were used any time error would result in a measured intensity error.

The square wave used is not a pure square wave but a near square wave having a rising and falling edge taking a finite time. The square wave generator 40 contains a pure square wave generator 40A the output of which is passed through a low pass filter 40B to generate the near square wave by which the light emitting diode 20 is driven. This near square wave waveform has a relatively slow rise and fall time and a flat upper and lower plateau.

The averaged amplitude values produced by the calculators 46 and 47 are supplied to a further calculator 50. Initially a zeroing measurement is taken with air only in the sensing region 4, and the resulting averaged amplitude values from the photodiodes 38 and 41 are stored in a memory 51. Then the sensor 1 is inserted into the exhaust pipe 2 and the engine run up to maximum speed and allowed to drop back to idle. The measurements taken during this testing cycle are all supplied to the calculator 50, which uses them and the air only readings held in the memory 51 and calculates the corrected proportional change in amplitude using the formula.

$$\text{Change} = \frac{A_E}{A_A} \times \frac{A_{MA}}{A_{ME}}$$

Where $A_A$ is the averaged amplitude measured by photodiode 38 with air in the sensing region 4.

$A_E$ is the averaged amplitude measured by photodiode 38 with exhaust gases in the sensing region 4.

$A_{MA}$ is the averaged amplitude measured by monitoring photodiode 41 when $A_A$ was measured.

$A_{ME}$ is the averaged amplitude measured by monitoring photodiode 41 when $A_E$ was measured.

This zeros the sensor 1 before each measurement in case the light transmission path 6 between the light emitting diode 20 and photodiode 41 has had its transmissivity changed, for example by dirt on or damage to the windows 23A and 23B.

The inclusion of the amplitudes from the monitoring photodiode 41 acts as a correction factor for fluctuations in the light intensity from the light emitting diodes, and because the photodiodes 38 and 41 have identical processing circuitry any changes due to temperature variation will tend to cancel out.

The processor 50 stores the highest change value over the testing cycle in the memory 51. The cycle is repeated twice more and the highest change value obtained over all three test cycles is stored in the memory 51.

Taking this highest change value the calculator 50 then uses it and data held permanently in the memory 51 to calculate the peak opacity of the gas within the sensing chamber 4. It then outputs this opacity value on a line 52 for display on a visual display unit (not shown) to the user.

The data permanently held in the memory 51 defines the relationship between changing amplitude with air and with exhaust gas and increasing opacity of the exhaust gases.

The electrostatic precipitator could be replaced by any other filter type, such as a mesh filter, to remove particles from the air used in the air curtains. A remote air intake, for example on the end of a flexible hose attached to the sensor, could be used to reduce the filtering required by obtaining relatively clean air away from the vehicle exhaust pipe. Alternatively where the sensor is used repeatedly in the same area, such as a testing station the compressor and filter could be omitted from the sensor and clean compressed air supplied by a hose from a fixed remote compressor and filter.

The use of a semiconductor header is preferred, but any other type of mounting could be used.

The use of three testing cycles is not essential, one cycle only or any other number could be used.

Instead of storing the highest change value produced in a number of cycles, the highest change value produced in each cycle could be averaged over a number of cycles.

The sensing portion 4A could be attached to the main body by one catch, or three or more catches rather than the two catches described if convenient.

The necessary commands to operate the system are given using a keypad, this can be mounted directly on the main body or on a remote keypad linked by a lead.

I claim:

1. An exhaust gas particle sensor comprising a light source and light sensor means in which the opacity of gas is measured by passing a light beam emitted by the light source through the gas and said particle sensor includes means for varying the intensity of the light beam emitted by the said light source in a near square wave waveform, said means for varying being coupled to said light source and comprising means for generating a pure square wave waveform and means for modifying said square wave waveform to produce said near square wave waveform as an output, said output being coupled to said light source.

2. A sensor as claimed in claim 1 where said particles are smoke particles.

3. A sensor as claimed in claim 1 in which the light sensor means comprises a first photodetector arranged to sense the intensity of said light beam before it is passed through the gas and a second photodetector arranged to sense the intensity of said light beam after it is passed through the gas.

4. The sensor of claim 1 wherein said means for modifying said square wave comprises a low pass filter.

5. A sensor as claimed in claim 3 in which each photodetector has its output sampled to produce a series of peak and trough output values which are then averaged over a set number of cycles.

6. A sensor as claimed in claim 5 where a rolling average of a set of number of cycles is maintained.

7. An exhaust gas particle sensor which measures the opacity of a gas by passing a light beam through the gas and measures the intensity thereof comprising:

a light emitting diode means for emitting the beam;

a first photodiode means coupled to said sensor for sensing the intensity of the beam after it has passed through the gas and a second photodiode means for sensing the intensity of the beam before it passes through the gas, said light emitting diode means being mounted on a header and the second photodiode means being mounted on a rigid extension of the same header so that a part of the light emitted by the light emitting diode means toward the gas is directly incident on the second photodiode means.

8. A sensor as claimed in claim 7 in which the header has a substantially planar surface and the rigid extension extends orthogonally to this surface.

9. A sensor as claimed in claim 7 in which the header is a semiconductor header.

* * * * *